(12) United States Patent
Hoey et al.

(10) Patent No.: US 8,911,430 B2
(45) Date of Patent: *Dec. 16, 2014

(54) MEDICAL PROBES FOR THE TREATMENT OF BLOOD VESSELS

(71) Applicant: Tsunami MedTech, LLC, Menlo Park, CA (US)

(72) Inventors: Michael Hoey, Shoreview, MN (US); John H. Shadduck, Menlo Park, CA (US)

(73) Assignee: Tsunami MedTech, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/032,009

(22) Filed: Sep. 19, 2013

(65) Prior Publication Data

US 2014/0018890 A1 Jan. 16, 2014

Related U.S. Application Data

(63) Continuation of application No. 12/486,702, filed on Jun. 17, 2009, now Pat. No. 8,579,888.

(60) Provisional application No. 61/132,242, filed on Jun. 17, 2008, provisional application No. 61/134,204, filed on Jul. 8, 2008.

(51) Int. Cl.
| | | |
|---|---|---|
| *A61B 18/18* | (2006.01) | |
| *A61B 18/04* | (2006.01) | |
| *A61B 19/00* | (2006.01) | |
| *A61F 7/12* | (2006.01) | |
| *A61F 2/95* | (2013.01) | |
| *A61B 18/24* | (2006.01) | |
| *A61B 17/00* | (2006.01) | |
| *A61B 18/00* | (2006.01) | |

(52) U.S. Cl.
CPC . *A61F 7/12* (2013.01); *A61B 18/18* (2013.01); *A61B 18/1815* (2013.01); *A61F 2/95* (2013.01); *A61B 18/24* (2013.01); *A61B 2017/00243* (2013.01); *A61B 2018/00011* (2013.01); *A61B 2018/1861* (2013.01)
USPC .................. 606/2; 606/14; 606/27; 128/898

(58) Field of Classification Search
USPC ........................................ 606/2–52; 128/898
See application file for complete search history.

(56) References Cited

U.S. PATENT DOCUMENTS

| 408,899 A | 8/1889 | Bloch et al. |
|---|---|---|
| 697,181 A | 4/1902 | Smith |

(Continued)

FOREIGN PATENT DOCUMENTS

| WO | WO 00/11927 | 3/2000 |
|---|---|---|
| WO | WO 00/29055 | 5/2000 |

(Continued)

OTHER PUBLICATIONS

Coda, et al., "Effects of pulmonary reventilation on gas exchange after cryolytic disobstruction of endobronchial tumors," *Minerva Medical*, vol. 72, pp. 1627-1631, Jun. 1981 (with English translation).

(Continued)

*Primary Examiner* — Dawayne A Pinkney
(74) *Attorney, Agent, or Firm* — Levine Bagade Han LLP

(57) ABSTRACT

Devices and methods for thermally-mediated treatment of blood vessels to elicit an immune response to cause rapid endothelial growth over at least portions of an implant or stent to prevent adverse events such as restenosis. Devices and methods for thermally-mediated treatment to inhibit contraction of vessels to elicit an immune response to cause rapid endothelial growth over at least portions of a stent to prevent adverse events such as restenosis.

19 Claims, 6 Drawing Sheets

(56) References Cited

U.S. PATENT DOCUMENTS

| | | |
|---|---|---|
| 1,719,750 A | 9/1927 | Bridge et al. |
| 3,818,913 A | 6/1974 | Wallach |
| 3,880,168 A | 4/1975 | Berman |
| 3,930,505 A | 1/1976 | Wallach |
| 4,024,866 A | 5/1977 | Wallach |
| 4,083,077 A | 4/1978 | Knight et al. |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,950,266 A | 8/1990 | Sinofsky |
| 4,985,027 A | 1/1991 | Dressel |
| 5,006,119 A | 4/1991 | Acker et al. |
| 5,011,566 A | 4/1991 | Hoffman |
| 5,084,043 A | 1/1992 | Hertzmann et al. |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,263,951 A | 11/1993 | Spears et al. |
| 5,277,696 A | 1/1994 | Hagen |
| 5,298,298 A | 3/1994 | Hoffman |
| 5,318,014 A | 6/1994 | Carter |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,669,907 A | 9/1997 | Platt, Jr. et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,735,811 A | 4/1998 | Brisken |
| 5,741,247 A | 4/1998 | Rizoiu et al. |
| 5,741,248 A | 4/1998 | Stern et al. |
| 5,752,965 A | 5/1998 | Francis et al. |
| 5,755,753 A | 5/1998 | Knowlton |
| 5,782,914 A | 7/1998 | Schankereli |
| 5,785,521 A | 7/1998 | Rizoiu et al. |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,836,896 A | 11/1998 | Rosenschein |
| 5,843,019 A | 12/1998 | Eggers et al. |
| 5,843,073 A | 12/1998 | Sinofsky |
| 5,871,469 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,913,856 A | 6/1999 | Chia et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwan |
| 5,989,445 A | 11/1999 | Wise et al. |
| 5,997,499 A | 12/1999 | Sussman et al. |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,056,746 A | 5/2000 | Goble et al. |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,106,516 A | 8/2000 | Bmassengill |
| 6,110,162 A | 8/2000 | Sussman et al. |
| 6,113,722 A | 9/2000 | Hoffman et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,194 A | 12/2000 | Eggers et al. |
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,206,848 B1 | 3/2001 | Sussman et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,654 B1 | 7/2001 | Swartz et al. |
| 6,277,112 B1 | 8/2001 | Underwood et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,296,636 B1 | 10/2001 | Cheng et al. |

(56) References Cited

U.S. PATENT DOCUMENTS

| | | |
|---|---|---|
| 6,296,638 B1 | 10/2001 | Davison et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |
| 6,315,755 B1 | 11/2001 | Sussman |
| 6,319,222 B1 | 11/2001 | Andrew et al. |
| 6,327,505 B1 | 12/2001 | Medhkour et al. |
| 6,331,171 B1 | 12/2001 | Cohen |
| 6,355,032 B1 | 3/2002 | Hovda et al. |
| 6,375,635 B1 | 4/2002 | Moutafis et al. |
| 6,379,350 B1 | 4/2002 | Sharkey et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,416,508 B1 | 7/2002 | Eggers et al. |
| 6,458,231 B1 | 10/2002 | Wapner et al. |
| 6,461,350 B1 | 10/2002 | Underwood et al. |
| 6,464,694 B1 | 10/2002 | Massengill |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,517,568 B1 | 2/2003 | Sharkey et al. |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,248 B1 | 4/2003 | Bass |
| 6,547,810 B1 | 4/2003 | Sharkey et al. |
| 6,558,379 B1 | 5/2003 | Batchelor et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B2 | 9/2003 | Underwood et al. |
| 6,623,444 B2 | 9/2003 | Babaev |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,755,794 B2 | 6/2004 | Soukup |
| 6,758,846 B2 | 7/2004 | Goble et al. |
| 6,763,836 B2 | 7/2004 | Tasto et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,674 B1 | 5/2005 | Woloszko et al. |
| 6,896,675 B2 | 5/2005 | Leung et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,918,903 B2 | 7/2005 | Bass |
| 6,921,385 B2 | 7/2005 | Clements et al. |
| 6,929,640 B1 | 8/2005 | Underwood et al. |
| 6,949,096 B2 | 9/2005 | Davison et al. |
| 6,955,675 B2 | 10/2005 | Jain |
| 6,960,182 B2 | 11/2005 | Moutafis et al. |
| 6,962,584 B1 | 11/2005 | Stone et al. |
| 6,972,014 B2 | 12/2005 | Eum et al. |
| 6,986,769 B2 | 1/2006 | Nelson et al. |
| 6,991,028 B2 | 1/2006 | Comeaux et al. |
| 6,991,631 B2 | 1/2006 | Woloszko et al. |
| 7,022,088 B2 | 4/2006 | Keast et al. |
| 7,031,504 B1 | 4/2006 | Argiro et al. |
| 7,083,612 B2 | 8/2006 | Littrup et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,192,400 B2 | 3/2007 | Campbell et al. |
| 7,233,820 B2 | 6/2007 | Gilboa |
| 7,235,070 B2 | 6/2007 | Vanney |
| 7,335,195 B2 | 2/2008 | Mehier |
| 7,347,859 B2 | 3/2008 | Garabedian et al. |
| 7,549,987 B2 | 6/2009 | Shadduck |
| 7,585,295 B2 | 9/2009 | Ben-Nun |
| 7,674,259 B2 | 3/2010 | Shadduck |
| 7,892,229 B2 | 2/2011 | Shadduck et al. |
| 8,016,823 B2 | 9/2011 | Shadduck |
| 2001/0020167 A1 | 9/2001 | Woloszko et al. |
| 2001/0029370 A1 | 10/2001 | Hodva et al. |
| 2001/0037106 A1 | 11/2001 | Shadduck |
| 2002/0049438 A1 | 4/2002 | Sharkey et al. |
| 2002/0077516 A1 | 6/2002 | Flanigan |
| 2002/0082667 A1 | 6/2002 | Shadduck |
| 2002/0095152 A1 | 7/2002 | Ciarrocca et al. |
| 2002/0111386 A1 | 8/2002 | Sekins et al. |
| 2002/0128638 A1 | 9/2002 | Chauvet et al. |
| 2002/0133147 A1 | 9/2002 | Marchitto et al. |
| 2002/0161326 A1 | 10/2002 | Sussman et al. |
| 2002/0177846 A1 | 11/2002 | Mulier et al. |
| 2002/0193789 A1 | 12/2002 | Underwood et al. |
| 2003/0028189 A1 | 2/2003 | Woloszko et al. |
| 2003/0040742 A1 | 2/2003 | Underwood et al. |
| 2003/0097126 A1 | 5/2003 | Woloszko et al. |
| 2003/0099279 A1 | 5/2003 | Venkatasubramanian et al. |
| 2003/0109869 A1 | 6/2003 | Shadduck |

(56) References Cited

U.S. PATENT DOCUMENTS

| | | |
|---|---|---|
| 2003/0130655 A1 | 7/2003 | Woloszko et al. |
| 2003/0130738 A1 | 7/2003 | Hovda et al. |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0212395 A1 | 11/2003 | Woloszko et al. |
| 2003/0225364 A1 | 12/2003 | Kraft et al. |
| 2004/0024398 A1 | 2/2004 | Hovda et al. |
| 2004/0024399 A1 | 2/2004 | Sharps et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0049180 A1 | 3/2004 | Sharps et al. |
| 2004/0054366 A1 | 3/2004 | Davison et al. |
| 2004/0055606 A1 | 3/2004 | Hendricksen et al. |
| 2004/0068256 A1 | 4/2004 | Rizoiu et al. |
| 2004/0068306 A1 | 4/2004 | Shadduck |
| 2004/0087937 A1 | 5/2004 | Eggers et al. |
| 2004/0116922 A1 | 6/2004 | Hovda et al. |
| 2004/0193150 A1 | 9/2004 | Sharkey et al. |
| 2004/0199226 A1 | 10/2004 | Shadduck |
| 2004/0230190 A1 | 11/2004 | Dahla et al. |
| 2004/0254532 A1 | 12/2004 | Mehier |
| 2005/0004634 A1 | 1/2005 | Ricart et al. |
| 2005/0010205 A1 | 1/2005 | Hovda et al. |
| 2005/0119650 A1 | 6/2005 | Sanders et al. |
| 2005/0166925 A1 | 8/2005 | Wilson et al. |
| 2005/0171582 A1 | 8/2005 | Matlock |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0267467 A1 | 12/2005 | Paul et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161233 A1 | 7/2006 | Barry et al. |
| 2006/0200076 A1 | 9/2006 | Gonzalez et al. |
| 2006/0224154 A1 | 10/2006 | Shadduck et al. |
| 2007/0036417 A1 | 2/2007 | Argiro et al. |
| 2007/0091087 A1 | 4/2007 | Zuiderveld |
| 2008/0033493 A1 | 2/2008 | Deckman et al. |
| 2008/0103566 A1 | 5/2008 | Mehier |
| 2008/0110457 A1 | 5/2008 | Barry et al. |
| 2008/0114297 A1 | 5/2008 | Barry et al. |
| 2008/0132826 A1 | 6/2008 | Shadduck et al. |
| 2009/0105702 A1 | 4/2009 | Shadduck |
| 2009/0105703 A1 | 4/2009 | Shadduck |
| 2009/0149846 A1 | 6/2009 | Hoey et al. |
| 2009/0216220 A1 | 8/2009 | Hoey et al. |
| 2009/0312753 A1 | 12/2009 | Shadduck |
| 2010/0076416 A1 | 3/2010 | Hoey et al. |
| 2010/0160905 A1 | 6/2010 | Shadduck |
| 2010/0204688 A1 | 8/2010 | Hoey et al. |
| 2010/0262133 A1 | 10/2010 | Hoey et al. |
| 2011/0077628 A1 | 3/2011 | Hoey et al. |
| 2011/0118717 A1 | 5/2011 | Shadduck |
| 2011/0160648 A1 | 6/2011 | Hoey |
| 2011/0264090 A1 | 10/2011 | Shadduck et al. |
| 2012/0065632 A1 | 3/2012 | Shadduck |
| 2012/0259271 A1 | 10/2012 | Shadduck et al. |

FOREIGN PATENT DOCUMENTS

| | | |
|---|---|---|
| WO | WO 02/069821 | 9/2002 |
| WO | WO 03/070302 | 8/2003 |
| WO | WO 03/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema," *N Engl J Med*, vol. 348, No. 21, pp. 2059-2073, May 22, 2003.

Homasson, et al., "Bronchoscopic cryotherapy for airway strictures caused by tumors," *Chest*, vol. 90, No. 2, pp, 159-164, Aug. 1986.

Li, K., "Efficient optimal net surface detection for image segmentation—from theory to practice," M.Sc. Thesis, The Universit of Iowa, 2003.

Marasso, et al., "Cryosurgery in bronchoscopic treatment of tracheobronchial stenosis" *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobrinchial argon plasma coagulation for treatment of hemotysis and neoplastic airway obstruction," *Chest*, vol. 119, No. 3, pp. 781-787, Mar. 2001.

Moulding et al., "Preliminary studies for achieving transcervical oviduct occlusion by hot water or low-pressure steam," *Advancesin Planned Parenthood*, vol. 12, No. 2; pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp, 1-17, 1994.

Tschirren et al.; "Intrathoracic airway trees: segmentation and airway morphology analysis from low-dose CT scans;" *IEEE Trans. Med. Imaging*, vol, 24, No. 12; pp, 1529-1539. Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.

Xia, Y. et al. "Soft Lithography," *Annu. Rev. Mater. Sci.*, vol. 28, pp. 153-184, 1998, accessed at http://www.bwfoundry.com/xia.pdf.

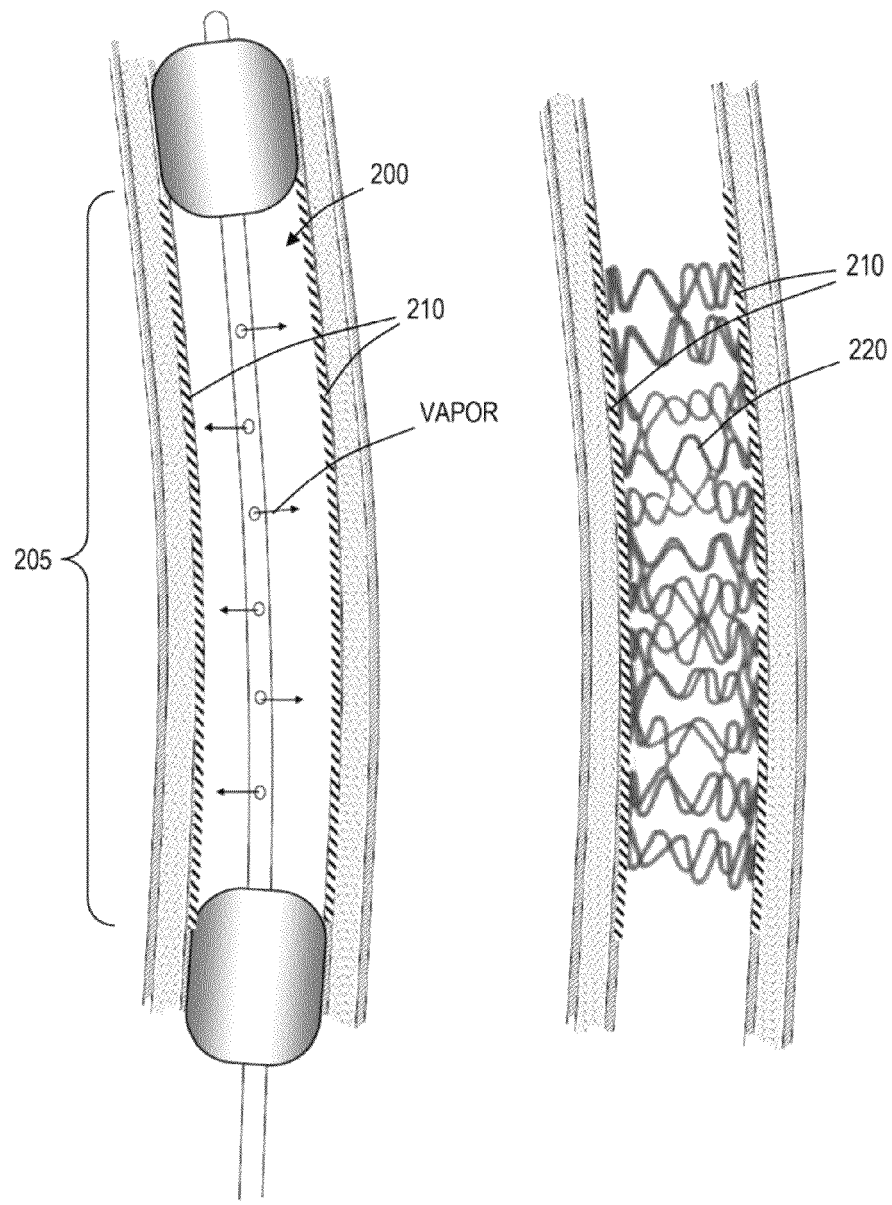
*FIG. 4A*  *FIG. 4B*

MEDICAL PROBES FOR THE TREATMENT OF BLOOD VESSELS

CROSS-REFERENCE TO RELATED APPLICATIONS

This application is a continuation of U.S. patent application Ser. No. 12/486,702 filed Jun. 17, 2009, which claims benefit of U.S. Patent Provisional Application Nos. 61/132,242, filed on Jun. 17, 2008 and 61/134,204, filed or Jul. 8, 2008, the content of each of which are incorporated herein by reference in their entirety.

BACKGROUND OF THE INVENTION

1. Field of the Invention

This invention relates to a medical probe or catheter with a working end configured for thermally-mediated treatment of blood vessels to elicit an immune response to cause rapid endothelial growth over at least portions of a stent to prevent adverse events such as restenosis.

2. Description of Related Art

A myocardial infarction is a form of disorder that is caused by a sudden lack of oxygen and nutrients to heart muscles. Myocardial infarction (MI) may account for as much as 20% of deaths in the U.S., and is a major cause of sudden death in adults. In the past, it was believed that MI was caused by arteriosclerosis or hardening of the arteries in coronary vessels which progressively closed the arteries to normal blood flow. More recently, it has been learned that sudden blockages of arteries, for example, by the rapture of cholesterol plaque can result in blood clotting and occlusion of an artery. In this case, the restricted blood flow will cause cellular damage to heart muscle downstream, which can be fatal. Another form of MI that can result in sudden death relates to vasospasm in coronary arteries. New systems and methods are needed for treating arteries to prevent vasospasm and other body structures to prevent muscle spasms.

BRIEF SUMMARY OF THE INVENTION

The following disclosure teaches the application of controlled energy delivery to tissue within the body to effect a therapeutic change. The therapeutic change can include affecting the ability of the body organ to contract or spasm. Alternatively, or in combination, the energy delivery can be applied to elicit an immune response in tissue.

With regard to a cardiovascular application, one variation of the method includes a method of reducing vasospasm in a blood vessel. As such, the method can include locating a target site within the blood vessel and applying an amount of thermal energy at the target site where the amount of thermal energy is sufficient to reduce an ability of a muscle in a blood vessel tissue to contract.

The amount of energy applied can be sufficient to inhibit a function of actomyosin in the tissue or results in a modification of contractile proteins in the tissue. Additionally, the energy can also desirably inhibit function of at least one of actin, myosin, myofilaments, titin filaments, nebulin filaments, and sarcomeric subunits in the tissue. In some cases it will be desirable to treat the target tissue only to affect or modify the tissue characteristics without actually ablating the tissue.

In the methods describe herein application of energy can be take the form of thermal energy (meaning energy that raises a temperature of the tissue). For example, such energy modalities include Rf energy, light energy, ultrasound, energy, resistive heating energy, inductive heating energy, mechanical energy and microwave energy as well as other resistive heating, inductive heating, conduction heating, or irradiation. In some examples, the application of energy is performed with light energy (coherent or non-coherent).

In another variation, applying energy to the tissue can include application of a flow media or vapor media to the target site and tissue. The flow media or vapor media comprises a heat of vaporization, where the flow media condenses at the target site to release the heat of vaporization to the blood vessel tissue causing an increase in temperature of the blood vessel tissue to reduce an ability of the muscle in the blood vessel tissue to contract. The introduction of the flow media or vapor media into the organ allows the media to change phase such that the change in phase delivers a selected level of energy to the tissue for the purposes described herein. Such treatment allows a physician to treat the tissue to reduce an ability of a muscle in the tissue to contract. Additional details regarding the application of a flow media or vapor media is found in the patent applications discussed below.

The application of energy can occur directly on the tissue or alternatively, the energy can be applied to an intermediate structure. For example, the method can include expanding a balloon in the target site and applying the energy within the balloon so that energy transfer occurs between the balloon and tissue but only the balloon surface contacts the tissue.

In additional variations it may be necessary to occlude or isolate a section the target tissue to control the treatment area. In such a case, the system or method can include the use of at least one balloon at the target site to occlude at least a portion of the target site. For example a single hour glass shaped balloon or multiple balloons can be used to isolate sections of the tissue that are distal and proximal to the target site.

The methods described above can be used in conjunction with any additional medical procedure. For example, when treating a blood vessel, the method can include performing an angioplasty within the blood vessel or deploying a stent in the blood vessel In an additional variation, the methods described herein can further include monitoring an electrical parameter of the tissue to effect treatment or to determine the outcome of the treatment. For example, the electrical parameter can comprises a capacitance, an impedance, a rate of change of capacitance, and a rate of change of impedance of the tissue. The method can further comprise comparing the electrical parameter to at least one data value from a library of values to determine an intended effect in the tissue.

The method can further include providing customization of treatment systems based on modeled data. For example, one method include determining a library of data of operation parameters for applying a selected level of energy to reduce an ability of a muscle in a blood vessel tissue to contract using a model energy delivery system having energy application means in a working end configured for applying energy to a wall of a body vessel; and providing the library of data for loading within a remote catheter system. The library of data can include a list or array of data that is associated with a known, or predictable result and can be correlated with real time parameters when used in a treatment system.

This disclosure also includes an additional variation for treating a vascular site where the method includes positioning a catheter working end in a treatment region in the vascular site, applying a selected level of energy at the working end of the catheter, wherein the selected level of energy elicits an immune response to cause substantially rapid endothelial growth in the treatment region.

The method of eliciting an immune response can be used in combination with deploying an implant in the treatment region where the selected level of energy causes substantially rapid endothelial growth over portions of the implant. For example, the implant can include a stent, aneurysm treatment device, or any other structure implanted within the vasculature. Such an implant can be positioned using the same device used to deliver the energy. Moreover, the treatment can occur prior to, during, and/or subsequent to placement of the implant.

The level of energy applied will vary depending upon such factors, including but not limited to, the severity of the disease at the site, the type of vessel, and size of the vessel, the rate of blood flow, the state of the tissue. However, in certain variations, the amount of energy applied comprises a de minimis amount of energy to elicit the immune response.

In order to provide an effective treatment, energy applications can apply the energy uniformly to a vessel wall at the treatment region. For example, the use of irradiation or flow/vapor media allows such uniform treatment. Additionally, applying the energy can include expanding an expandable structure at the working end of the catheter and wherein the expandable structure applies the selected level of energy. For example, the expandable member can be a balloon in which energy is released. In some variations, the balloon can serve to normalize energy delivery about the surface of the balloon.

As with the previous methods, the treatment region can be occluded or isolated so that application of energy occurs in the isolated site. One or more balloons can be used to isolate the site.

As also noted above, the treatment methods can be combined with other therapeutic or interventional procedures.

The methods can further include measuring a biological characteristic of tissue of the treatment region to aid in the treatment or to adjust the level of energy applied. In one example, measurement of the characteristic can include applying electrical current to tissue to measure the characteristic or an electrical parameter of the tissue. Such characteristics are described above. In these cases, the measurement can occur using an electrode located on the device, a balloon on the device, or on an implant that is intended for deployment at the site.

Another variation for providing the treatments described herein includes a catheter system for treating a vascular site, comprising an elongated catheter having a working end that carries a deployable stent, and an energy delivery section located at the working end, where the energy delivery section is configured to applying uniform energy to elicit an immune response about the working end to uniformly treat tissue adjacent to a region in which the stent is deployed.

In another variation, a device for carrying out the treatments described herein can include an expandable stent configured for deployment in an endoluminal or other site; and at least a pair of electrodes spaced apart in a surface of a body of the expandable stent, where the electrodes are coupleable to a power supply and are configured to measure at least one electrical parameter of tissue in the site. The device can include one or more electrodes for characterizing or measuring tissue parameters. The electrodes can be located on the device, on the stent, or on a balloon that is used to occlude or expand the stent.

Another variation of the method includes determining a parameter of a region of tissue by contacting the region of tissue with an electrode arrangement configured to create an electrical circuit in the region tissue, applying current to create an electrical circuit in the region tissue, and utilizing a controller capable to determine at least one of capacitance or impedance to derive a value, and comparing the value with at least one library value selected from a library of data stored in a controller to determine the parameter.

Such a method can be used in a variety of body organs. For example, the region of tissue can include the lining of a uterus and the parameter can include a thickness of endometrium.

The library of data can include data that allows determination of a parameter of the region of tissue. Such data can include data previously on heat capacity, thermal diffusion characteristic, heat sink characteristic, fluid content or mobility, depth of the region of tissue, volume of the region of tissue, cross section of the region of tissue, hydration of the region of tissue, geometry of the region of tissue, and blood flow.

In another variation, the method can include determining a library of data of operation parameters for applying a selected level of energy to elicit an immune response to cause substantially rapid endothelial growth in a treatment region using a model catheter system having energy application means in a working end configured for applying energy to a wall of a body vessel, and providing the library of data for loading within a remote catheter system.

Another variation of a method of vascular treatment includes providing a catheter system having a working end with a balloon and light energy application means expanding the balloon in a treatment site without stretching the vessel wall; applying a selected level of light energy to weaken disulphide bonds and/or hydrogen bonds in collagen without raising the temperature of the collagen tissue sufficient to cause collagen denaturation; and allowing said bonds to reform about the expanded balloon to thereby remodel the treatment site.

The following features of a stent can be combined with of the methods, systems and/or devices described herein: constructed from biodegradable, bioabsorbable or bioexcretable materials; the stent can include any drug-eluting substance; the stent can be fabricated from a metallic alloy, a shape memory alloy, a polymeric composition, or other bio-compatible material.

The methods and devices disclosed herein can be used to treat a variety of body organs where application of energy is used to inhibit a contraction-type response of the body organ or for eliciting a desired immune response. Accordingly, while the current disclosure teaches use of the device and methods within the vasculature of a body, the methods and devices, can also be applied to various body lumens and passages, for example: the cardiovascular system such as within or around heart or vasculature; the respiratory system (the lungs, upper and lower airways, parenchyma), the digestive system (the esophagus, stomach, digestive tract, etc.).

In variations of the method and systems described above, the application of energy can range from at least 1200 kJ/kg, 1300 kJ/kg, 1400 kJ/kg, 1500 kJ/kg, 1600 kJ/kg, 1700 kJ/kg, 1800 kJ/kg, 1900 kJ/kg and 2000 kJ/kg. In another aspect, the controller can be configured to apply energy of less than 10000 Joules, 5000 Joules, 1000 Joules, 500 Joules, 100 Joules and 10 Joules. Moreover, the treatment duration can range from intervals of less that 60 seconds, 30 seconds, 20 seconds, 10 seconds and 5 seconds.

All patents, patent applications and publications mentioned in this specification are herein incorporated by reference to the same extent as if each individual publication or patent application was specifically and individually indicated to be incorporated by reference.

BRIEF DESCRIPTION OF THE SEVERAL VIEWS OF THE DRAWINGS

FIG. 4A is an illustration of a catheter working end configured for vapor delivery intermediate first and second occlusion balloons to create an immune response to induce rapid endothelial growth over stent struts.

FIG. 4B is an illustration of a stent deployed in the treatment site treated by vapor delivery in FIG. 4A.

DETAILED DESCRIPTION OF THE INVENTION

The following description of the certain embodiments of the invention is illustrative in nature, and as such it does not limit in any way the present invention or its methods of use. Modifications may be made by those skilled in the art without departing from the true spirit and scope of the invention. In addition, the disclosure is intended to include combinations of the device, systems and methods described herein as well as combinations of embodiments or aspects of the embodiments themselves. The following illustrations are intended to convey an overall concept of the inventive methods, systems and devices.

As used in the specification, "a" or "an" means one or more. As used in the claim(s), when used in conjunction with the word "comprising", the words "a" or "an" mean one or more. As used herein, "another" means as least a second or more. "Substantially" or "substantial" mean largely but not entirely. For example, substantially may mean about 10% to about 99.999, about 25% to about 99.999% or about 50% to about 99.999%.

Figure 1:
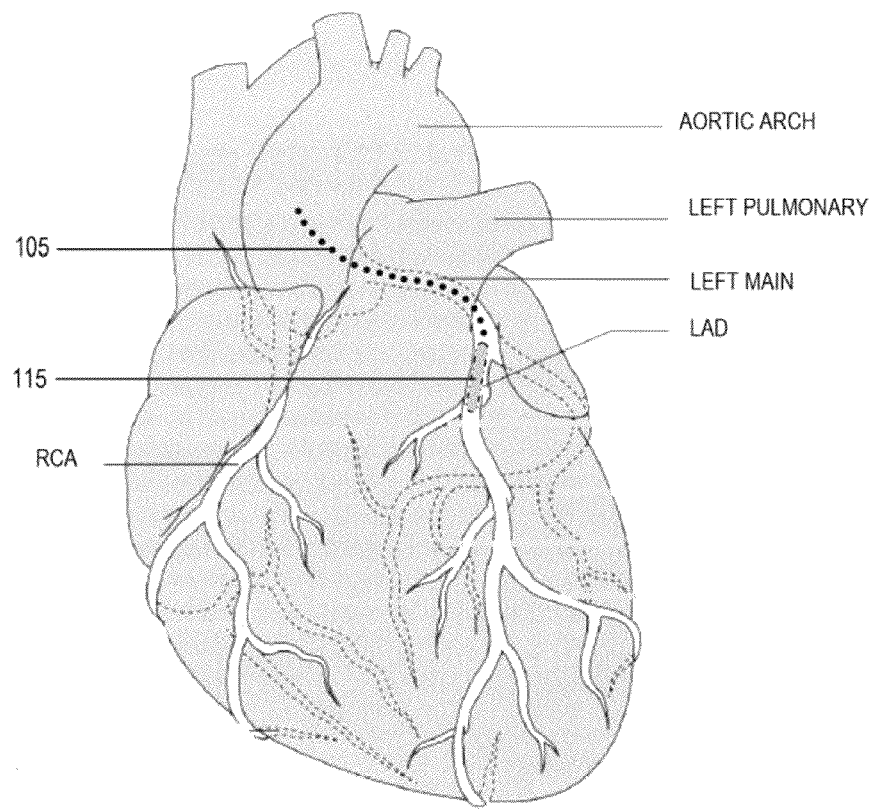
FIG. 1 is an illustration of a heart and blood vessels that may be a target of treatment with the system of the invention.
Figure 2:
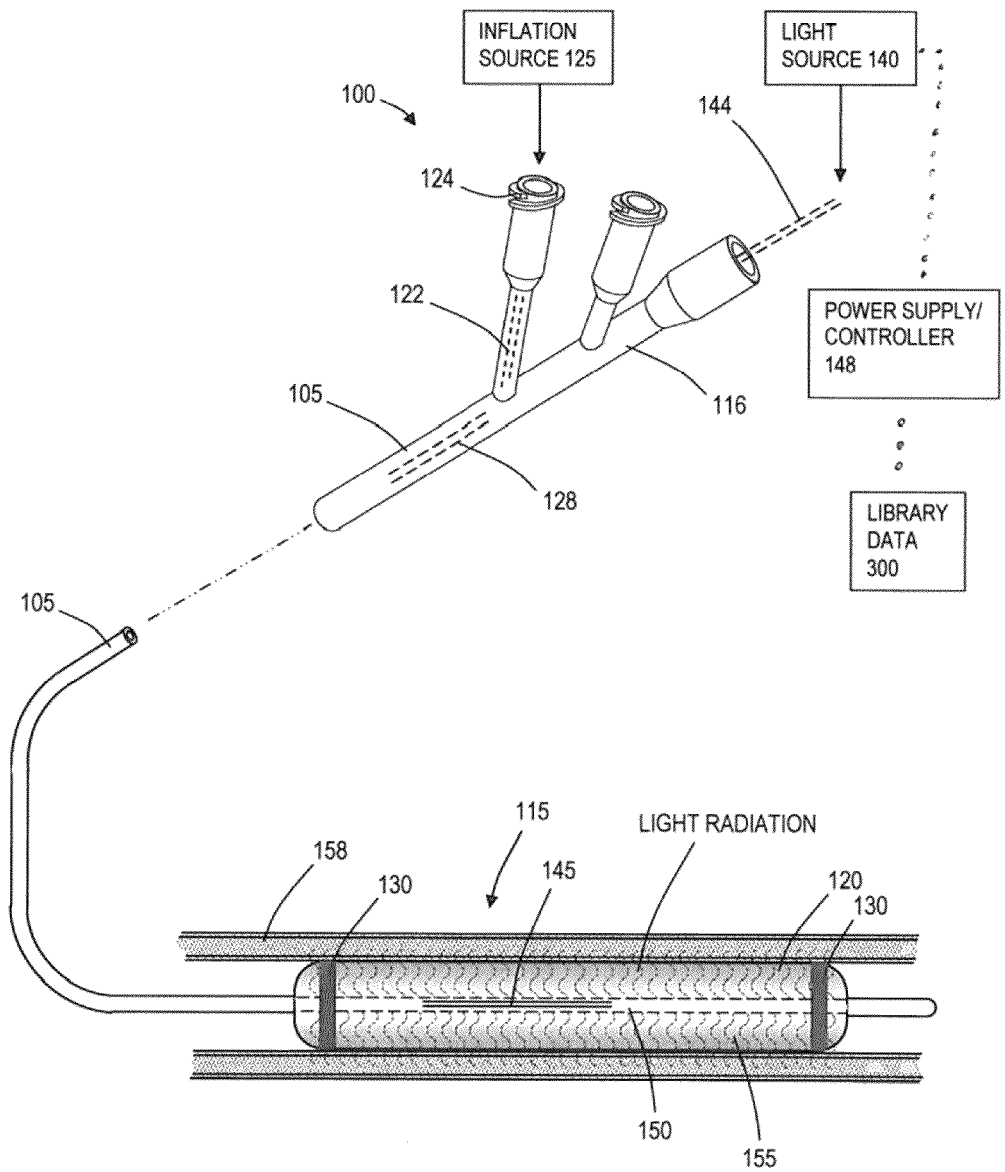
FIG. 2 is an illustration of a light energy thermal energy emitter for treating a blood vessel to prevent vasospasm.

FIG. 1 represents an example of an energy delivery catheter 100, with elongated catheter shaft 105 and working end 115 being advanced and positioned in a targeted site is a coronary artery, as an example a left anterior descending artery LAD. Referring to FIG. 2, this variation of the catheter or device 100 includes a proximal handle or hub portion 116 affixed to the proximal end of shaft 105 and a distal inflatable balloon 120 that is affixed to the working end 115 of the shaft 105. The shaft 105 defines at least two passageway or lumens, one of which is configured as an inflation lumen 122 connected to an interior chamber of balloon 120 for selectively inflating and deflating the balloon. The inflation lumen 122 has a proximal hub inflation port 124 comprising a coupling or Luer-lock fitting for connecting a source 125 of pressurized inflation fluid thereto (not shown) in the conventional manner.

Another lumen 128 defined by catheter 100 can function is a guidewire lumen and is adapted to receive an elongated flexible guidewire therein. A guidewire and catheter 100 may thus be advanced or withdrawn independently, or catheter 100 may be directed through the path first navigated by guidewire (not shown).

The catheter shaft 105 can be constructed with inner and outer tubular portions to define an annular space that functions as an inflation lumen and the guidewire lumen can be central to an inner tubular portion of the shaft. Alternatively, the catheter shaft can be a multi-channel extrusion. The shaft can be a suitable polymer material, such as a high density polyethylene (HDPE), polytetrafluoroethylene (PTFE), a nylon or a polyether block amide (PEBA).

The balloon 120 shown in FIG. 2 can be non-compliant or compliant and define any suitable inflated diameter and working length for a particular treatment. FIG. 2 shows the balloon configured with radiopaque markers 130 to indicate the position and working length of the balloon using any type of non-invasive imaging (such as fluoroscopy, x-ray, ultrasound, etc.)

FIG. 2 further depicts a light source 140 and optic fiber 144 configured for advancing to the working end 115 of the catheter in lumen 128 or another dedicated lumen. The optic fiber has a distal end 145 that allows for light emission from sides thereof as in known in the art. The catheter body portion 150 within the balloon is transparent to the selected wavelengths of light used for application of energy to the tissue. The balloon wall 155 similarly is transparent to the selected wavelengths. The wavelengths may be in the visible range or the infrared range. In certain variations, the optic fiber 144 and light source 140 can be replaced with any type of light source that generates the required energy within the balloon. For example, the fiber 144 can be replaced with a filament that, when powered, provides energy at a selected wavelength. In another variation, the fiber 144 can be replaced with a light emitting diode (LED) or conventional light source that is powered by a power supply (either within the device or in place of light source 140).

FIG. 2 also illustrates a power supply or controller 148 coupled to the energy source (in this case the light source 140). In certain variations of the system, the power supply 148 can receive library data 390 or information regarding tissue parameters. Such information can include capacitance and/or impedance values for comparison of measured values to determine a biological characteristic of the contacted tissue. The library can be configured for determining a biological characteristic selected from the group of heat capacity of tissue, thermal diffusion characteristics of tissue, heat sink characteristics of tissue, fluid content or mobility of tissue, depth of a type of tissue, volume of a tissue, cross section of a tissue in a lumen, hydration of a tissue, geometry of a tissue, and blood flow in a tissue.

The library data 300 can contain values for biological characteristics of tissues selected of from the group of tissues of a sinus, a nasal passageway, an oral cavity, a blood vessel, an arteriovascular malformation, a heart, an airway, a lung, a bronchus, a bronchiole, a lung collateral ventilation pathway, a larynx, a trachea, a Eustachian tube, a uterus, a vaginal canal, a cervical canal, a fallopian tube, an esophagus, a stomach, a liver, a duodenum, an ileum, a colon, a rectum, a bladder, a prostate, a urethra, a ureter, a vas deferens, a kidney, a gall bladder, a pancreas, a bone, an interior of a bone, a joint capsule, a tumor, a plexus of dilated veins, a fibroid, a neoplastic mass, brain tissue, skin, adipose tissue, an ovary, a cyst, a cornea and a retina.

The treatment described herein can be used to supplement other treatment modalities. For example, the balloon 120 of FIG. 2 can be used to perform an angioplasty procedure or other dilation based procedure within the blood vessel lumen (or other body organ in which the procedure takes place). In addition, the balloon 120 can be used to deliver a stent (not shown.) Clearly, the stent must allow sufficient radiation to pass to the treatment region. Therefore, the system can include use of a stent where the stent struts are spaced sufficiently to allow radiation or other energy to pass therethrough. Alternatively, the balloon 120 can be axially oversized in relation to the stent so that one or more ends of the balloon will not be covered by a stent structure and can therefore convey energy to the tissue. In yet another variation, the radiopaque markers 130 of the balloon 120 of FIG. 2 can also configured or wired in such a way as to form an electrical circuit between markers 130. Such a configuration allows the markers to also serve as electrodes (either single pole or opposite polarity) to form a circuit with the tissue and a power supply 148. In this configuration, the balloon 120 and electrodes 130 can obtain electrical or other parameters about the tissue for use as described below.

In general, blood vessels as well as other organs that have the ability to contract include smooth muscle and smooth muscle cells, see e.g., the vessel wall 158 of FIG. 2. The smooth muscle includes a system of actin and myosin that, along with other proteins and substances, constitutes muscle fiber and is responsible for muscular contraction or spasm. Myofibrils are cylindrical organelles found within muscle cells and consist of bundles of actomyosin filaments that run from one end of the cell to the other and are attached to the cell surface membrane at each end. Such actomyosin motors are important in muscle contraction as well as other processes like retraction of membrane blebs. The filaments of myofibrils, or myofilaments, consist of two types, thick and thin. Thin filaments consist primarily of the protein actin, coiled with nebulin filaments. Thick filaments consist primarily of the protein myosin, held in place by titin filaments. This protein complex composed of actin and myosin is sometimes referred to as "actomyosin." In striated muscle, such as skeletal and cardiac muscle, the actin and myosin filaments each have a specific and constant length on the order of a few micrometers, far less than the length of the elongated muscle cell (a few millimeters in the case of human skeletal muscle cells). The filaments are organized into repeated subunits along the length of the myofibril. These subunits are called sarcomeres. The muscle cell is nearly filled with myofibrils running parallel to each other on the long axis of the cell. The sarcomeric subunits of one myofibril are in nearly perfect alignment with those of the adjacent myofibrils. This alignment gives rise to certain optical properties which cause the cell to appear striped or striated. In smooth muscle cells, this alignment is absent. Hence, there are no apparent striations and the cells are called smooth.

In one variation under the present disclosure, a method includes damaging contractile proteins without substantial ablation or cell death in the remainder of the vessel wall. Thus, one method of reducing vasospasm at a particular vessel site comprises the steps of determining an amount of a thermal energy which will have an intended inhibition of actin or myosin function, and applying thermal energy at the particular vessel site to inhibit at least one of muscle contraction and muscle spasm. The method can apply energy by means of light energy. The light energy can be coherent or non-coherent, and have an application interval or be pulsed. In one embodiment, the light energy is emitted within a balloon with a transparent wall that engages the vessel, wall as depicted in FIG. 2. The light energy can be applied over an interval of less than 5 minutes, 1 minute, 30 seconds and 10 seconds.

Figure 3A:
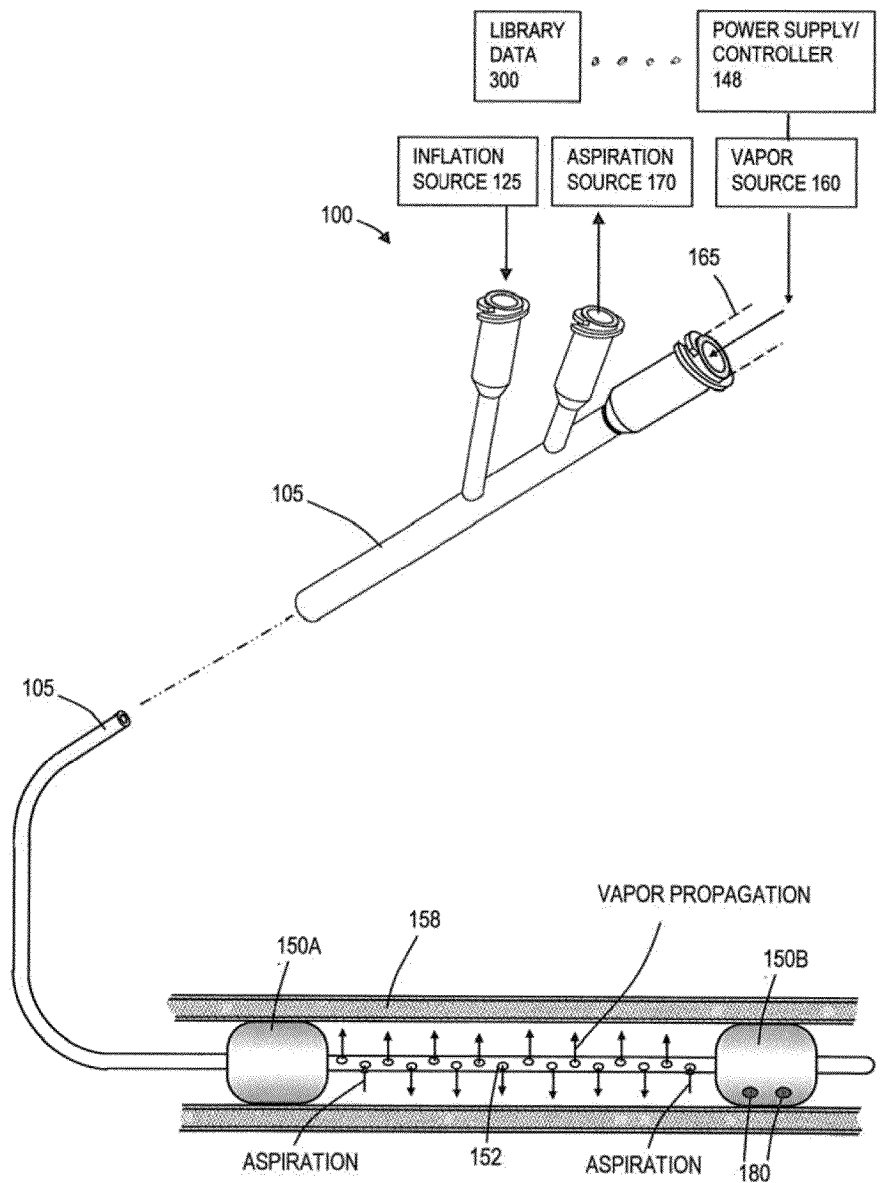
FIG. 3A is an illustration of a vapor delivery catheter for treating a blood vessel to prevent vasospasm.

In another variation of a method, damage to contractile proteins can be accomplished with energy applied by the release of the heat of vaporization from condensation of flow media introduced into the vessel lumen as shown in FIG. 3A. This method applies energy between occlusion balloons 150A and 150B in FIG. 3A from vapor source 160 coupled to catheter 165. Though the figure illustrates two balloons 150A and 150B a single balloon having two expandable portions can be used (e.g., an hour-glass design, a distensible balloon with a restraining sleeve over the center portion along treatment region 205, or a non-distensible balloon having the shape shown in FIG. 3).

The vapor can be delivered after aspiration of blood from the treatment site by means of aspiration source 170. The catheter shaft 105 has multiple lumens for balloon inflation, aspiration and vapor delivery and well as ports 152 in the working end for aspiration of blood and injection of vapor. Although FIG. 3A illustrates vapor propagation from each port 152. Any number of ports 152 can be independently fluidly coupled with a lumen that is fluidly coupled to the inflation source 125, aspiration source 170, or vapor source 160. Accordingly, one or more of the ports 152 can be used to expand a balloon member, aspirate fluids from the site, or deliver the vapor/flow media.

Figure 3B:
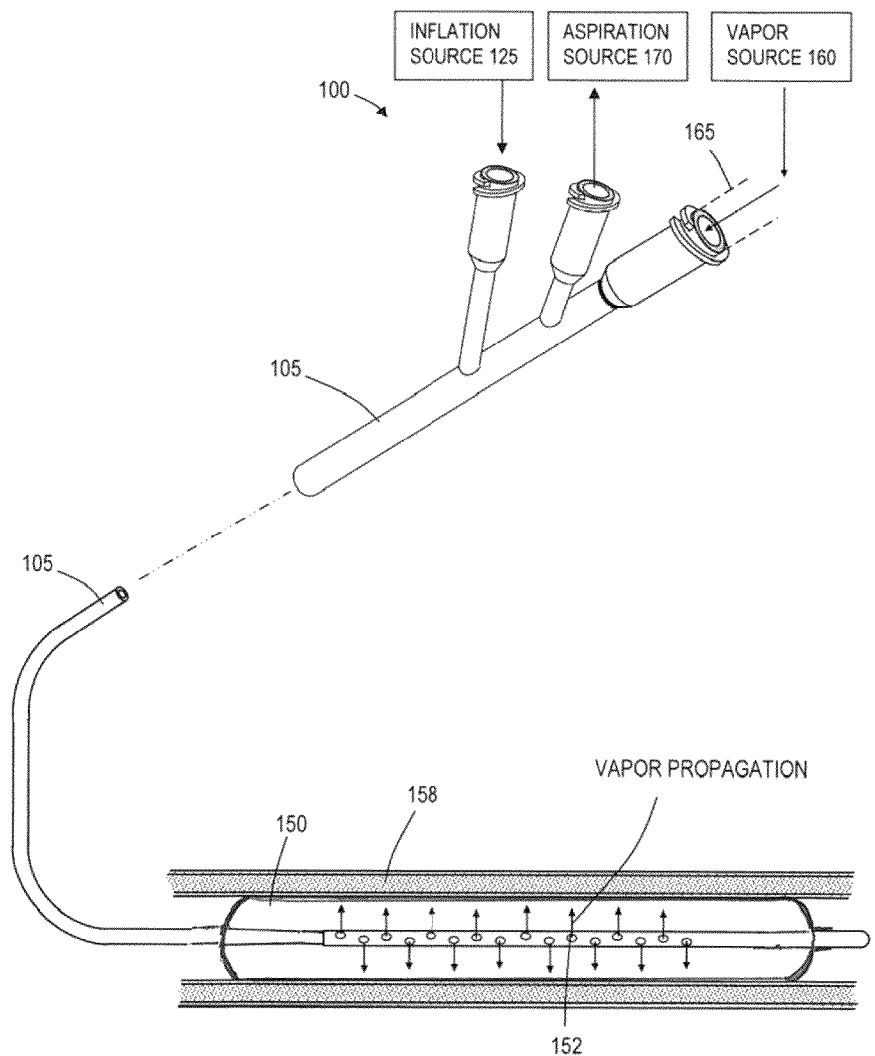
FIG. 3B is an illustration of a vapor delivery catheter for delivering a flow media or vapor into a balloon within a blood vessel or other lumen.

In contrast to FIG. 3A, FIG. 3B illustrates a balloon 150 that directly engages a wail of the vessel 158. The flow media is released into the balloon through ports 152 so that the balloon surface transfers the energy to the tissue. In certain variations, the inflation lumen can be fluidly isolated from ports 152. In other variations, the ports 152 that deliver the flow media can also be used to inflate the balloon 150 and aspirate the residual flow media.

It has been found that vapor can be used to provide highly uniform energy delivery about the vessel lumen, with various aspects and features of vapor delivery tools disclosed In the following issued patents or co-pending applications of the authors, which are incorporated herein by reference in their entirety as if provided in full text herein:

U.S. Pat. No. 6,911,028 issued Jun. 28, 2005 titled "Medical Instrument Working End and Method for Endoluminal Treatments"; U.S. Pat. No. 6,508,816 issued Jan. 21, 2003 titled "Medical Instrument Working End Creating Very High Pressure Gradients"; U.S. Pat. No. 6,210,404 issued Apr. 3, 2001 titled "Microjoule Electrical Discharge Catheter for Thrombolysis in Stroke Patients"; U.S. Pat. No. 6,669,694 issued Dec. 30, 2003 titled "Medical Instruments and Techniques for Highly-Localized Thermally-Mediated Therapies"; U.S. patent application Ser. No. 10/681,625 filed Oct. 7, 2003 titled "Medical Instruments and Techniques for Thermally-Mediated Therapies" (published Apr. 8, 2004 as US 2004/0068306); U.S. patent application Ser. No. 10/830,372 filed Apr. 22, 2004 titled "Thermotherapy Device With Superlattice Cooling" (published Oct. 7, 2004 as US 2004/0199226); U.S. Patent Application Ser. No. 60/615,900 filed Oct. 5, 2004 titled "Medical Instruments and Techniques for Thermally-Mediated Procedures"; U.S. Patent Application Ser. No. 60/643,045 filed Jan. 11, 2005 titled "Surgical Instrument and Method of Use"; U.S. patent application Ser. No. 11/158,930 filed Jun. 22, 2005 titled "Medical Instruments and Techniques for Treating Pulmonary Disorders"; U.S. patent application Ser. No. 11/244,329 filed Oct. 5, 2005 titled "Medical Instruments and Methods of Use"; U.S. patent application Ser. No. 11/329,381 filed Jan. 10, 2006 titled "Medical Instrument and Method of Use"; U.S. patent application Ser. No. 12/167,155 tiled Jul. 2, 2003 titled "Medical System and Methods of Use; and U.S. patent application Ser. No. 12/389,808 filed Feb. 20, 2009 titled "Medical System and Method of Use.

In another variation of a method, damage to contractile proteins can be accomplished with energy applied by vapor condensation within an interior chamber or a balloon which then conducts thermal energy to the vessel wall.

In general, a method of inhibiting vasospasm in a patient comprises delivering vapor to a vessel of the patient, and causing modification of contractile proteins in a vessel wall. The vapor is delivered and energy is applied endoluminally.

More in general, a method of treating target tissue within a lumen of a patient's body comprise introducing an elongate energy delivery tool into the lumen, delivering vapor from the tool into the lumen; and modifying actomyosin function to inhibit spasm in a wall of the lumen.

A method of providing a therapeutic effect in a body structure can include comfortably applying energy to targeted muscle tissue sufficient to inhibit function of contractile proteins to prevent contraction or spasm of said muscle tissue. The applied energy is non-ablative to the body structure. The method can further include performing an angioplasty and can include stent deployment.

A method of providing a therapeutic effect can include determining the amount of thermal energy required to control muscle contraction in a vessel portion, and applying said thermal energy at a particular vessel site to provide an intended reduction muscle contraction. The applied energy is selected to inhibit function of at least one of actomyosin, actin, myosin, myofilaments, thin, filaments, nebulin filaments, and sarcomeric subunits. The applied energy can extend for an interval of less that 60 seconds, 30 seconds, 20 seconds, 10 seconds and 5 seconds. The applied energy is less than 10000 joules, 5000 Joules, 1000 Joules, 500 joules, 100 Joules and 10 Joules.

In general, a method of providing a therapeutic effect can comprise applying a selected level of energy to the vessel wall sufficient to inhibit function of contractile proteins wherein the applied energy provided by at least one of electromagnetic energy, mechanical energy and chemical energy, and more particularly can be provided by at least one of phase change energy release, Rf energy, light energy, ultrasound energy, resistive heating energy, inductive heating energy and microwave energy.

In one method of providing such therapeutic effect with vapor, the applied energy can be provided by a phase change of media that has a vapor content versus liquid droplet content of at least 50%, 60%, 70%, and 80%.

In another method of providing such therapeutic effect with vapor, the media can provide applied energy of at least 1200 kJ/kg, 1300 kJ/kg, 1400 kJ/kg, 1500 kJ/kg, 1600 kJ/kg, 1700 kJ/kg, 1800 kJ/kg, 1900 kJ/kg and 2000 kJ/kg.

In another method of providing such therapeutic effect, the method can include monitoring capacitance or impedance of tissue in the vessel wall, and determining an intended effect in the tissue based on said capacitance or impedance. The monitoring step can comprise creating an electrical circuit in the tissue, measuring a value of at least one of the capacitance or impedance, change of capacitance or impedance or rate of change of capacitance or impedance of the tissue, and determining an intended effect in the tissue based on comparison to a library of values of previously characterized tissue.

Another method comprises a method consisting of providing a heat applicator system configured for applying energy to a body vessel, determining system operation parameters for applying energy sufficient to inhibit function of contractile proteins to prevent contraction or spasm of muscle tissue in a vessel wall, and collaboratively or independently, marketing or commercializing a system for treating blood vessels.

Another method comprises providing a heat applicator system configured for applying energy to a body vessel and an electrical applicator system configured for measuring the capacitance of vessel tissue, determining system operation parameters for applying energy sufficient to inhibit function of contractile proteins to prevent contraction or spasm of muscle tissue in a vessel wall and for determining a treatment effect based upon said capacitance, and collaboratively or independently, marketing or commercializing a system for treating blood vessels.

Another method of providing a therapeutic effect in a body structure comprise controllably applying energy to targeted muscle tissue selected from the group of smooth muscle, striated muscle, skeletal muscle and cardiac muscle sufficient to inhibit function of contractile proteins to prevent contraction or spasm of said muscle tissue. The method can provide an intended affect selected from the class of inhibiting vascular restenosis, inhibiting vasospasm, inhibiting MI, inhibiting stroke, inhibiting wrinkles, inhibiting BPH, inhibiting airway disorders, inhibiting disorders of sinuses, inhibiting disorders of the arterial or venous systems, inhibiting disorders of the heart, inhibiting disorders of the esophagus, inhibiting disorders of the oral cavity, inhibiting disorders of the gastrointestinal tract, inhibiting diabetic disorders, inhibiting disorders of structures of a male reproductive system and inhibiting disorders of structures of a female reproductive system.

In general, the invention comprises a medical system for treating a vessel wail that comprises a probe having a proximal end and a working end and energy application means carried by the working end configured for controlled application of energy to muscle tissue is the vessel wall to inhibit function of contractile proteins to prevent contraction or spasm of said muscle tissue. The system can carry at least one expandable structure at a working end. The system has energy application means that can comprise a light source coupled to at least one optic fiber emitter configured to emit light energy at the working end. In another embodiment, the energy application means can comprise a source of vapor in communication with at least one outlet in the working end, wherein the vapor is configured to condense to thereby deliver the heat of vaporization to the vessel wall. In any embodiment, the system further comprised a controller for controlling an operational parameter of the applied energy. The controller is capable of controlled application of energy of at least 1200 kJ/kg, 1300 kJ/kg, 1400 kJ/kg, 1500 kJ/kg, 1600kJ/kg, 1700 kJ/kg, 1800 kJ/kg, 1900 kJ/kg and 2000 kJ/kg. In another aspect, the controller is configured to apply energy of less than 10000 Joules, 5000 Joules, 1000 joules, 500 joules, 100 Joules and 10 joules, in another aspect, the controller is configured to apply energy for an interval of less that 60 seconds, 30 seconds, 20 seconds, 10 seconds and 5 seconds.

In another embodiment, the system comprises an electrode structure 180 (FIG. 3A) in an expandable structure configured for creating an electrical circuit in the vessel wall, and a controller capable of analyzing current in the tissue to determine at least one of capacitance or impedance, change of capacitance or impedance or rate of change of capacitance or impedance to determine an intended effect in the tissue. As shown, the electrodes can be spaced apart Systems and Methods for Stent-Related and Other Treatments In another system and method, a catheter system with a working end 200 as depicted in FIGS. 4A-4B is provided to prevent restenosis in a location of a deployed stent. One method of the invention for treating a vascular site comprises positioning a catheter working end 200 in a treatment region 205 in a vascular site and actuating an energy application means in the working end wherein a selected level of applied energy elicits an immune response to cause substantially rapid endothelial growth in the treatment region. In FIGS. 4A-4B the treated region and tissue that results in the immune response is indicated at 210. The method further comprise deploying a stent 220 in the treatment region and the applied energy and elicited immune response causes a substantially rapid endothelial growth over the struts of the stent thus preventing blood contact with the stent which it is believed will prevent local thrombus formation, restenosis and other adverse events without using drug elation from the stent in an attempt to prevent such adverse events.

The method of the invention as depicted in FIGS. 4A-4B includes utilizing a de minimis selected level of applied energy that does not cause neointimal hyperplasia. The method utilizes a selected level of applied energy does not modify the intima, media and adventitia of the vascular site.

Still referring to FIGS. 4A-4B, the method applies the selected level of energy uniformly to the vessel walls of a treatment region, or in other words, in 360 degrees about the treatment region to elicit the immune response uniformly. Further, the method delivers energy in a treatment region that is configured to extend beyond first and second ends of the stent 220. In one method, the energy is delivered by a vapor as described previously. In another method, the energy can be delivered from a light source though a light-transmissible wall of a balloon. In general, the applied energy can be provided by at least one of a phase change energy release of a vapor, Rf energy, light energy, LED means, ultrasound energy, resistive heating energy, inductive heating energy and microwave energy.

In general, a method for treating a vascular site comprises positioning a catheter working end in a targeted treatment region in the vascular site, deploying a stent carried by the working end in the treatment region and applying uniform energy about the treatment region thereby eliciting an immune response wherein the immune response causes endothelial growth over at least portions of the stent. The deployment of the stent can precede the applying energy step or the applying energy step can precede the stent deploying step.

In one method, the applied uniform energy is less than 10000 Joules, 5000 Joules, 1000 Joules, 500 Joules, 100 Joules and 10 Joules. In one method, the applied uniform energy extends for an interval of less that 60 seconds, 30 seconds, 20 seconds, 10 seconds and 5 seconds.

In another method of the invention, the applying energy step includes the step of measuring a biological characteristic of tissue of the treatment region. In one method, the measuring step includes applying an electrical current to the tissue to measure at least one of tissue capacitance and/or impedance. The applying current step can include applying current from at least one electrode in a surface of a balloon. Alternatively, the applying current step can include applying current from at least one electrode in a surface of the stent. In this method, the stent can be at least partly of a metal, or can be at least one of biodegradable, bioabsorbable or bioexcretable. The stent can be a balloon-deployable stent or a self-expanding stent. The stent also can be a drug-eluting type of stent. In another embodiment, the stent can be fabricated of a light transmissible polymer material that substantially allows light transmission from a light source at the interior of a balloon to thus allow light energy to propagate substantially uniformly to the vessel wall to cause the intended therapeutic effect as described above.

Figure 5A:
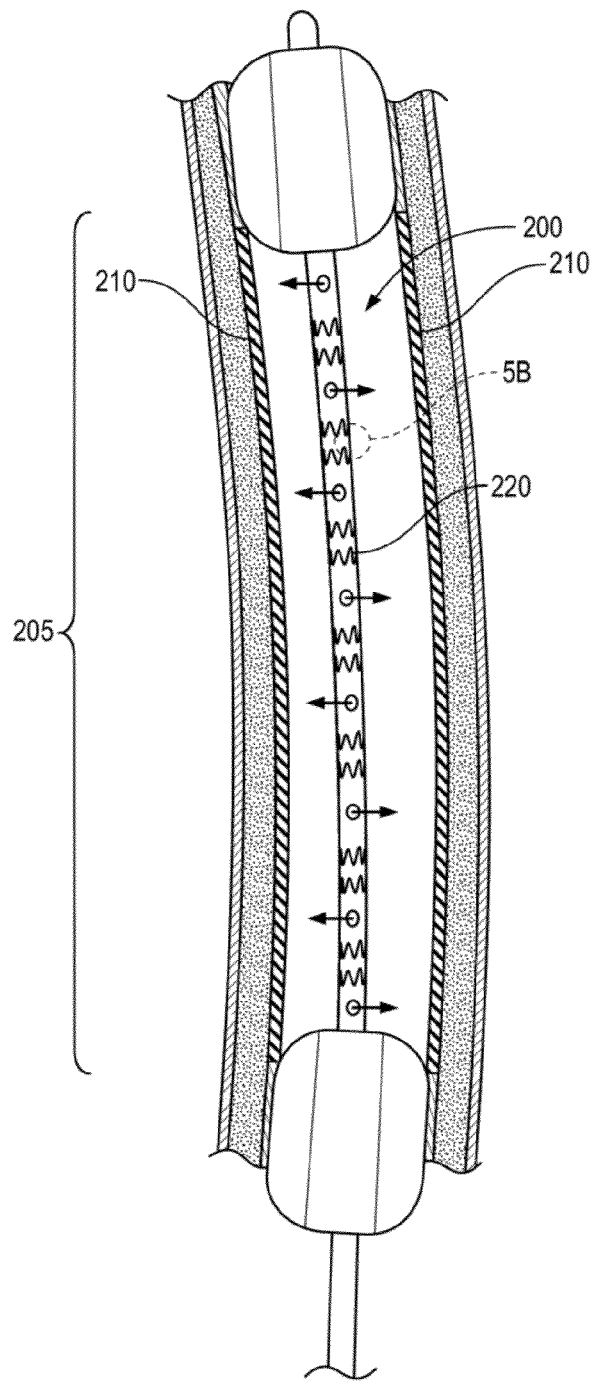
FIG. 5A is an illustration of a catheter working end configured for energy delivery with one or more occlusion balloons and a deployable stent or implant on the catheter.

FIG. 5A shows a catheter working end 200 configured for energy delivery with one or more optional occlusion balloons and a deployable stent or implant 220 on the catheter. As noted herein, the energy delivery modality can be incorporated on the catheter 200 so that the stent 220 does not interfere with delivery of energy to the tissue. The stent or implant 220 can be a self expanding implant or can incorporate a balloon member for expansion. The energy delivery can occur before, after, and/or during deployment. The stent configuration shown in FIG. 5A can be combined with any energy delivery modality described above.

Figure 5B:
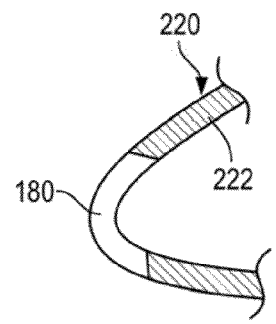
FIGS. 5B and 5C illustrate additional implant configurations having electrodes.
Figure 5C:
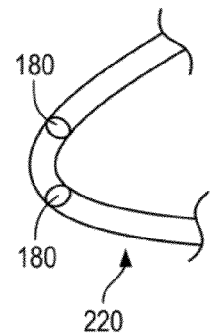

FIGS. 5B and 5C illustrate another aspect for use with the methods, systems and devices described herein. In this variation, the stent or implant 220 can be configured with electrodes 180 or can be part of the electrical circuit and thus function as an electrode. In most cases, the stent 220 will be placed against tissue either prior to deployment of any occlusion balloon if any parameters of the tissue are to be measured prior to treatment. However, when configured with electrode 180, the implant 220 can take measurements after deployment. The number of electrodes 180 on the implant 220 can vary as needed. However, FIG. 5B illustrates an example where a portion of the implant 220 includes a coated or covered area 222. In order for this configuration to function as an electrode, the implant 220 is electrically conductive and coupled to a power supply through conventional means. The uncovered portion 180 functions as an electrode. FIG. 5C illustrates the state where a stent 220 is non-conductive (e.g., formed from a polymer or metal not conducive to functioning as an electrode). In these cases, an electrode material can be deposited on or in a surface or body of the implant. The electrical coupling to the electrodes 180 can be fabricated as detachable contacts so that the stent remains implanted while the catheter is removed. For example, the electrical circuit can be completed through capacitive coupling of the electrodes through a wall of the balloon on the catheter.

The electrodes can be spaced to contact tissue but where electrode pairs are spaced apart by less than 100 times the mean cell dimension in the contacted tissue, by less than 50 times the mean cell dimension in the contacted tissue, by less than 20 times the mean cell dimension in the contacted tissue and by less than 10 times the mean cell dimension in the contacted tissue. The medical system can carry the electrode arrangement in a working end or a probe or in the surface of a balloon, or on the implant as shown.

In general, a catheter system for treating a vascular site comprises an elongated catheter having a working end that carries a deployable stent and energy application means within the working end configured for applying uniform energy about a stent deployment region to elicit an immune response. The catheter system can be configured with energy application means selected from the group consisting of a phase change energy release system, an Rf energy system, a light energy system, an LED system, an ultrasound energy system, a resistive heating system, an inductive heating system and a microwave energy system. In one embodiment, the catheter system further comprises a controller for controlling an interval of energy application or for controlling an energy dose. The controller can be configured to provide a dose of less than 10000 Joules, 5000 Joules, 1000 Joules, 500 Joules, 100 Joules and 10 Joules and/or configured to provide an energy application interval of less that 60 seconds, 30 seconds, 20 seconds, 10 seconds and 5 seconds. The catheter system also can include at least one interior channel for aspirating fluid from a targeted treatment region (not shown in FIG. 4A).

As described above, a catheter system can be configured for measuring an electrical parameter of tissue in an endoluminal site, and further the expandable endoluminal stent can carry at least one spaced apart electrode arrangement in a surface of the stent body for measuring the electrical parameter of the tissue in the endoluminal site. The at least one spaced apart electrode arrangement can be in a non-conductive polymer surface portion of the stent body. Alternatively, the spaced apart electrode arrangement can be in a polymer stent body. The electrodes can be spaced apart by less than 5 mm, 2 mm, 1 mm, and 0.5 mm. The system further comprises an electrical source and controller coupled to the at least one spaced apart electrode arrangement. In one embodiment, the electrical source can be operatively coupled to the at least one spaced apart electrode arrangement by at least one electrical contact in a balloon surface. In another embodiment, the electrical source can be operatively coupled to the at least one spaced apart electrode arrangement by capacitive coupling through a wall of a balloon. The electrodes can axially spaced apart or radially spaced apart or both.

In one method, a parameter of a uterine lining in determined by the following steps: contacting the uterine tissue with an electrode arrangement configured to create an electrical circuit in uterine tissue, applying current to create an electrical circuit in the tissue, and utilizing a controller capable to determine at least one of capacitance or impedance to derive a value, and comparing the value with a library to determine the parameter. The parameter can be a thickness of an endometrium. The method can determine the parameter in a plurality of locations in the uterus. The parameter determined can be at least one of heat capacity of the tissue, thermal diffusion characteristics of the tissue, heat sink characteristics of the tissue, fluid content or mobility of the tissue, depth of the tissue, volume of a the tissue, cross section of the tissue, hydration of the tissue, geometry of the tissue, and blood flow in the tissue.

In general, a method of determining a parameter of a tissue targeted for ablation c an comprise contacting the targeted tissue with an electrode arrangement configured to create an electrical circuit in the tissue, applying current to create an electrical circuit in the tissue, and utilizing a controller capable to determine at least one of capacitance or impedance to derive a value, and comparing the value with a library to determine the parameter. As described above, the library can be configured for determining at least one parameter such as the group of heat capacity of tissue, thermal diffusion characteristics of tissue, heat sink characteristics of tissue, fluid content or mobility of tissue, depth, of a type of tissue, volume of a tissue, cross section of a tissue in a lumen, hydration of a tissue, geometry of a tissue, and blood flow in a tissue. The targeted tissue can be selected from the group of tissues of a sinus, a nasal passageway, an oral cavity, a blood vessel, an arteriovascular malformation, a heart, an airway, a lung, a bronchus, a bronchiole, a lung collateral ventilation pathway, a larynx, a trachea, a Eustachian tube, a uterus, a vaginal canal, a cervical canal, a fallopian tube, a liver, an esophagus, a stomach, a duodenum, an ileum, a colon, a rectum, a bladder, a prostate, a urethra, a ureter, a vas deferens, a kidney, a gall bladder, a pancreas, a bone, an interior of a bone, a joint capsule, a tumor, a plexus of dilated veins, a fibroid, a neoplastic mass, brain tissue, skin, adipose tissue, an ovary, a cyst, an eye, a cornea and a retina. The method can further comprise applying energy to the targeted, tissue to cause an intended therapeutic effect. The method of can further comprise determining the parameter of a tissue during the step of applying energy at least one of continuously, intermittently or in an interval between a plurality applying energy steps.

Another method of lung treatment can comprise contacting airway wall tissue with an electrode arrangement configured to create an electrical circuit in the tissue, applying current to create an electrical circuit in the tissue, and utilizing a controller capable to determine at least one of capacitance or impedance to derive a value, and comparing the value with a library to determine the parameter. The method can comprise determining the parameter in a plurality of locations in the airway wall. The library can be configured, for determining a level of applied energy for thermally modifying airway wall tissue, for example to cause a surface ablation of the airway wall tissue in a lung volume reduction surgery. The library can provide data determining a level of applied energy for shrinking collagen in airway wall tissue, for selecting an energy dose of an energy-laden vapor for causing an intended effect in the airway wall tissue or for selecting a duration of vapor delivery for causing the intended effect in the airway wall tissue.

Another method for prostate treatment for BPH or prostate cancer comprises contacting prostate tissue with an electrode arrangement configured to create an electrical circuit in the tissue, applying current to create an electrical circuit in the tissue, and utilizing a controller capable to determine at least one of capacitance or impedance to derive a value, and comparing the value with a library to determine the parameter. The library can provide data for determining a level of applied energy for thermally modifying the prostate tissue or for selecting an energy dose of an energy-laden vapor for causing an intended effect in the prostate tissue.

Another method of fibroid treatment comprises contacting fibroid tissue with an electrode arrangement configured to create an electrical circuit in the tissue, applying current to create an electrical circuit in the tissue, and utilizing a controller capable to determine at least one of capacitance or impedance to derive a value, and comparing the value with a library to determine the parameter. The library can provide data for determining a level of applied energy for thermally ablating the fibroid tissue or for selecting an energy dose of an energy-laden vapor for causing an intended effect in the tissue.

Another method of tumor treatment comprises contacting tumor tissue with an electrode arrangement configured to create an electrical circuit in the tissue, applying current to create an electrical circuit in the tissue, and utilizing a controller capable to determine at least one of capacitance or impedance to derive a value, and comparing the value with a library to determine the parameter. The library can provide data for determining a level of applied energy for thermally ablating the tumor tissue or for selecting an energy dose of an energy-laden vapor for causing an intended effect in the tissue. The tumor can be in a liver, breast, bone, brain, lung, bladder, gall bladder, pancreas, lymph node or any other location in a body.

In general, one method of stenting a vascular site, comprised deploying a stent from a catheter in a targeted treatment region of vasculature, introducing a selected vapor media into the treatment region through the catheter and allowing the vapor media to change phase thereby releasing the heat of vaporization and applying a selected level of energy to the treatment region to elicit an immune response that causes a substantially rapid endothelial growth over portions of the stent. The method can introduce the vapor media at a flow rate of ranging from 0.001 to 20 ml/min, 0.010 to 10 ml/min, 0.050 to 5 ml/min. The method can introduce the vapor media at an inflow pressure ranging from 0.5 to 1000 psi, 5 to 500 psi, and 25 to 200 psi. The method can provide the selected level of energy over an interval that is less than 60 seconds; less than 30 seconds, and less than 10 seconds. The method can further include introducing a second vapor media for altering that average mass temperature of the combined vapor media.

In general one method for treating an abnormal vascular site comprises positioning a catheter working end in a targeted treatment region in vasculature, expanding at least one working end expandable structure in the treatment region, introducing flowable media into the treatment region and converting the media from a first phase to a second phase thereby controllably applying energy to the treatment region sufficient to elicit an immune response. The expanding step can expands a balloon which expands a stent. The conversion of the media from vapor phase to liquid phase can occur within a fluid-tight balloon or within a porous balloon. The converting step is configured to elicit an immune response that causes substantially rapid endothelial growth over the struts of the stent. The converting step can include the conversion of a saline media from vapor phase to liquid phase or can use sterile water.

A business method according to the invention comprises providing a catheter system having energy application means in the working end configured for applying energy to a wall of a body vessel, determining system operation parameters for applying a selected level of energy to elicit an immune response to cause substantially rapid endothelial growth in a treatment region and collaboratively or independently, marketing or commercializing the catheter system.

Another business method comprises providing a catheter system having a working end with energy application means and stent deployment means, determining system operation parameters for applying a selected level of energy to elicit an immune response to cause substantially rapid endothelial over the stent and collaboratively or independently, marketing or commercializing the catheter system.

Systems and Methods for Remodeling Vascular Tissue

Another system, treatment method and business method relates to the above inventions and is adapted for remodeling vascular tissue. In one embodiment, a catheter is provided that has a working end configured with a balloon with light-transmissible walls and sources that can provide at least one of first and second wavelengths of light energy that are selected to be absorbed by (i) hydrogen bonds in collagen types in vessel wails and (ii) disulphide bonds in collagen types in vessel walls. Disulphide bonds and hydrogen bonds are covalent links between pairs of certain amino acids found in collagens. In human cells, there may be many different proteins that contain disulphide bonds and hydrogen bonds. These bonds have been generally considered to be either structural or catalytic. In collagen, structural bonds stabilize the protein. A method of the invention for remodeling vascular tissue comprises expanding a transparent balloon in an endovascular site, irradiating the vessel wall from a light emitter in the interior of the balloon, wherein the fluence and wavelength (e.g., about 1.4 to about 2.6 microns) is selected to temporarily affect the disulphide bonds and hydrogen bonds but the irradiation will not raise the temperature of the collagen tissue sufficient to cause collagen denaturation or shrinkage and will not raise the temperature so high as to cause damage to the vascular wall tissue. The balloon is expanded gently to displace blood and not to expand the lumen or damage tissue. After termination of energy delivery, the balloon remains inflated as the collagen bonds reform in the new shape to provide the remodeling. In one embodiment, the balloon can have a cooling fluid circulating therein either during energy delivery or after energy delivery.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

We claim:

1. A method of treating a muscle in a blood, vessel to reduce vasospasm in the blood vessel, the method comprising:
   locating a target site within the blood vessel; and
   applying an amount of thermal energy at the target site where the amount of thermal energy is sufficient to reduce an ability of a muscle in a blood vessel tissue to contract, where applying the thermal energy comprises applying a flow media to the target site where the flow media comprises a heat of vaporization, where the flow media condenses at the target site to release the heat of vaporization to the blood vessel tissue causing an increase in temperature of the blood vessel tissue to reduce an ability of the muscle in the blood vessel tissue to contract.

2. The method of claim where the thermal energy is sufficient to inhibit a function of actomyosin in the blood vessel tissue.

3. The method of claim 1, wherein the thermal energy is sufficient to inhibit function of at least one of actin, myosin, myofilaments, titin filaments, nebulin filaments, and sarcomeric subunits in the blood vessel tissue.

4. The method of claim 1. where applying thermal energy comprises applying an energy mode selected from the group consisting of Rf energy, light energy, ultrasound energy, resistive heating energy, inductive heating energy, mechanical energy and microwave energy.

5. The method of claim 1, where applying thermal energy comprises irradiating the target site with light energy.

6. The method of claim 1, further comprising expanding a balloon in the target site and applying the thermal energy within the balloon.

7. The method of claim 1, further comprising expanding a balloon at the target site and where applying the thermal energy comprises applying the flow media within the balloon.

8. The method of claim 1, wherein, delivering the flow medial comprises delivering a vapor to the blood vessel to cause modification of contractile proteins in the blood vessel wall.

9. The method of claim 1, where the flow media comprises a vapor content versus liquid droplet content of at least 50%.

10. The method of claim 1, where the flow media comprises a heat of vaporization of at least 1200 kJ/kg.

11. The method of claim 1, where applying the flow media comprises introducing an energy delivery device into the blood vessel, and delivering a vapor from the energy delivery device into the blood vessel.

12. The method of claim 1, wherein applying energy comprises applying energy uniformly about a wall of the blood vessel lumen.

13. The method of claim 1, wherein applying the amount of thermal energy comprises applying the amount of thermal energy to inhibit the function of actomyosin in the blood vessel without ablating the blood, vessel tissue.

14. The method of claim 1, further comprising performing an angioplasty within the blood vessel.

15. The method of claim 1, further comprising deploying a stent in the blood vessel.

16. The method of claim 1, where applying the amount of thermal energy comprises
   introducing a vapor media into the blood vessel and allowing the vapor media to change phase such that the change in phase delivers a selected level of energy to the blood vessel tissue to reduce an ability of a muscle in a blood vessel tissue to contract.

17. The method of claim 16, where introducing the vapor media comprises introducing the vapor media into a balloon located within the blood vessel.

18. The method of claim 16, further including expanding at least one occlusion balloon in the blood vessel to create an occluded region and where introducing the vapor media into the blood vessel comprises introducing the vapor into the occluded region.

19. A method comprising:
determining a library of data of operation parameters for applying a selected level of energy to reduce an ability of a muscle in a blood vessel tissue to contract using a model energy delivery system having an energy application portion in a working end configured for applying thermal energy to a wall of a body vessel, where applying the thermal energy comprises applying a flow media to the target site where the flow media comprises a heat of vaporization, where the flow media condenses at the target site to release the heat of vaporization to the blood vessel tissue causing an increase in temperature of the blood vessel tissue to reduce an ability of the muscle in the blood vessel tissue to contract; and
providing the library of data for loading within a remote catheter system.

* * * * *